United States Patent [19]

Johns

[11] Patent Number: 4,563,570

[45] Date of Patent: Jan. 7, 1986

[54] BATTERY POWERED CAUTERY WITH IMPROVED PROTECTIVE COVER ARRANGEMENT

[75] Inventor: David L. Johns, Clearwater, Fla.

[73] Assignee: Suncoast Medical Manufacturing, Inc., Clearwater, Fla.

[21] Appl. No.: 647,057

[22] Filed: Sep. 4, 1984

[51] Int. Cl.$^4$ .................. H05B 1/02; H01C 10/26; A61B 17/38
[52] U.S. Cl. .................. 219/240; 30/140; 128/303.1; 219/233; 219/533; 338/150
[58] Field of Search ............. 219/233, 235, 240, 533; 128/303.1, 303.14, 303.18; 30/140; 338/150, 152

[56] References Cited

U.S. PATENT DOCUMENTS

| | | | |
|---|---|---|---|
| 3,234,356 | 2/1966 | Babb | 219/233 X |
| 3,613,682 | 10/1971 | Naylor | 219/240 |
| 3,978,312 | 8/1976 | Barton et al. | 219/233 |
| 4,108,181 | 8/1978 | Saliaris | 219/240 X |
| 4,359,052 | 11/1982 | Staub | 219/233 X |

FOREIGN PATENT DOCUMENTS 1185558 3/1970 United Kingdom ............... 219/233

Primary Examiner—A. Bartis
Attorney, Agent, or Firm—Arthur W. Fisher, III

[57] ABSTRACT

A battery operated cautery includes a cylindrical housing configured to retain a voltage source, such as a plurality of batteries, and an electrically heated cautery tip carried by the front end of the housing and adapted to be selectively energized from the power source by a manually operable switch on the housing. The switch includes a contact element having rear end connected to a terminal of the power source and a front end movable into and out of engagement with a terminal electrode of the electrically heated tip to make and break the circuit between the tip and the power source by a operation of a depressible switch actuator on housing. A removable safety cover configured to mount on the front of the housing encloses the switch actuator and heating tip to prevent inadvertent switch actuation and to protect the tip when the cautery is being stored or transported. The safety cover includes an electrical insulating member which projects into the housing to a position between the front end of the movable contact element and the terminal electrode of the tip when the cover is mounted on the housing to mechanically lock the switch actuator against depression and to positively electrically insulate the front end of the contact element from the tip terminal electrode, thereby preventing inadvertent energization of the electrically heated tip. A rotatably adjustable variable resistor may be mounted on the rear end of the housing to allow the temperature of the heated tip to be selectively varied.

8 Claims, 7 Drawing Figures

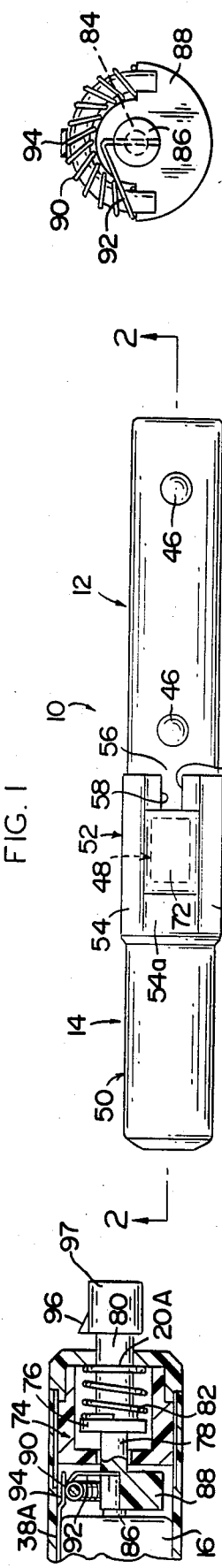
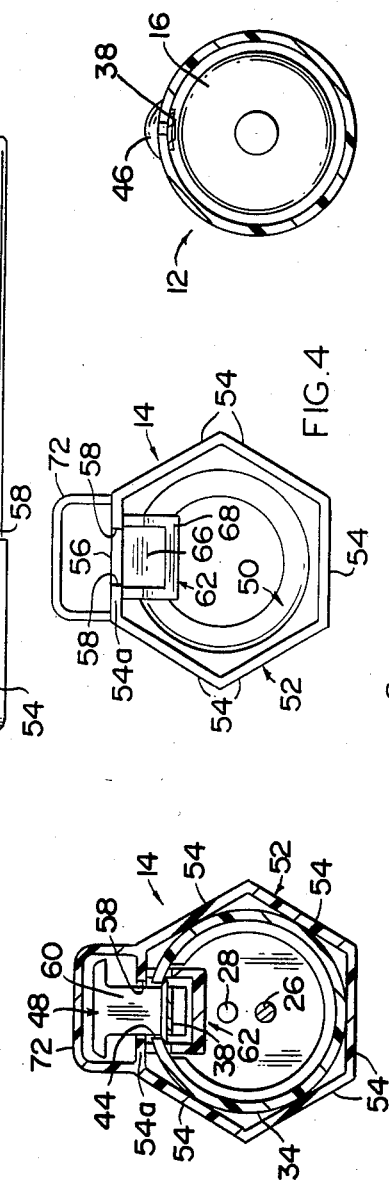
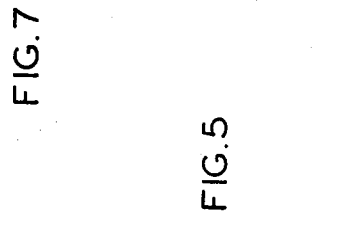
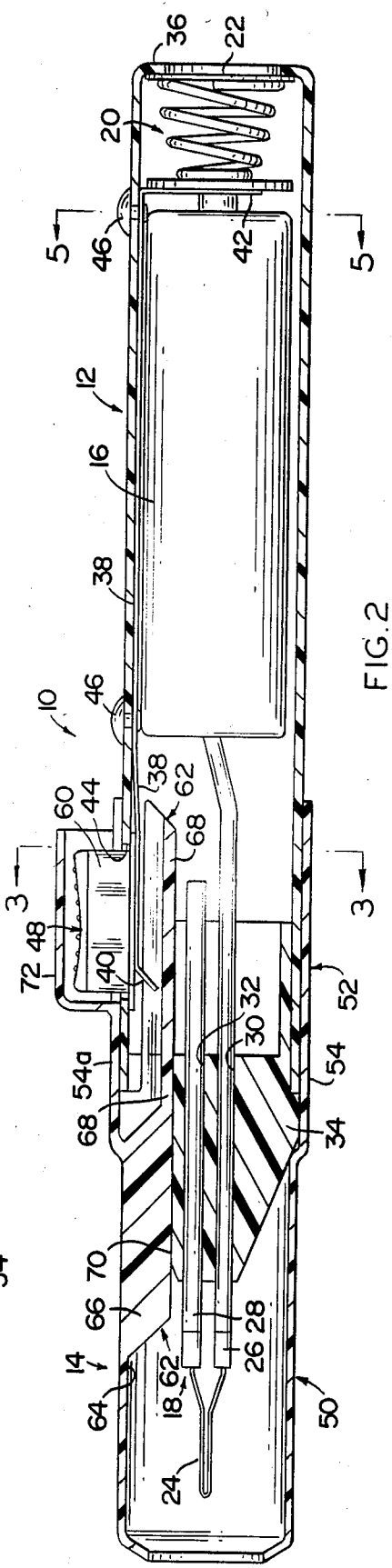

BATTERY POWERED CAUTERY WITH IMPROVED PROTECTIVE COVER ARRANGEMENT

BACKGROUND OF THE INVENTION

1. Field of the Invention

A battery operated cautery comprising a housing having an switch actuator mounted thereon and a removable cautery safety cover to prevent inadvertant actuating of the battery operated cautery.

2. Description of the Prior Art

Various disposable, self-contained, variable temperature, battery operated, cautery and similar hand held devices have been developed.

Typically a heated-wire electrode tip is operatively mounted to a tubular or hollow housing configured to retain a voltage source therein. A switch actuator is provided to selectively energize or actuate the electrode tip. A removable protective cover is often provided to avoid inadvertant switch actuation. To insure that the protective cover does not become dislodged from the housing, a locking or safety mechanism may be provided.

Examples of electrically operated hand tools are shown in U.S. Letters Pat. Nos. 1,366,756; 2,120,598; 2,224,464; 2,310,844; 2,994,324; 3,141,087; 3,141,956; 3,152,590, 3,234,356; 3,424,165; 3,526,750; 3,558,854; 3,662,151; 3,830,226; 3,881,468; 3,886,944; 3,919,522; and 3,978,312.

However, in order to enhance safety and operation of such cautery, the present invention improves the safety without decreasing operational efficiency.

SUMMARY OF THE INVENTION

The present invention relates to a battery operated cautery comprising a substantially cylindrical enclosure having a removable safety cover removably mounted thereon.

The substantially cylindrical enclosure is configured to retain a voltage source comprising one or more batteries in series biased to engage a cautery heating element. The cautery heating element comprises a heating tip extending outwardly from a pair of electrodes that pass through a retainer member. As described more fully hereinafter, the retainer member or cautery heating element retainer is welded or fixedly secured to the substantially cylindrical enclosure.

A conductor member including a first and second contact element formed on opposite ends thereof is operatively housed within the substantially cylindrical enclosure. The conductor member is axially aligned with the longitudinal dimension of a switch actuator aperture formed on the substantially cylindrical enclosure is fixed in position by fastening means disposed at opposite ends thereof. A switch actuator at least partially disposed within the switch actuator aperture is fixed to the forward portion of the conductor member immediately adjacent the first contact element. The conductor member, movable between a first and second position, is normally disposed in the first position out of operative engagement with the second electrode.

When the removable safety cover is operatively mounted on the substantially cylindrical enclosure, the cautery heating element and the actuator switch are housed therein. The removable safety cover further includes an insulating means comprising an insulating member extending inwardly from the inner sidewall thereof including an angled portion and a parallel portion. The insulating means is configured to pass through a conduit or channel formed in the cautery heating element retainer to normally be disposed between the first contact element and the second electrode when the removable safety cover is operatively mounted on the substantially cylindrical enclosure.

In operation, the battery operated cautery is normally stored and transported with the removably safety cover operatively mounted or attached to the substantially cylindrical enclosure. Further, the insulating means further prevents contact between the first contact element and second electrode.

When in use, the removable safety cover is removed from the substantially cylindrical enclosure to permit actuation of the switch actuator by depression from the first to second position such that the first contact element engages the second electrode completing the electrical circuit to selectively actuate the cautery heating element. The circuit is completed since the second contact element engages the first terminal of the voltage source or battery and the first electrode engages the second terminal of the voltage source or battery.

The invention accordingly comprises the features of constructions, combination of elements and arrangement of parts which will be exemplified in the construction hereinafter set forth, and the scope of the invention will be indicated in the claims.

DESCRIPTION OF THE DRAWINGS

For a fuller understanding of the nature and objects of the invention, reference should be had to the following detailed description taken in connection with the accompanying drawings in which:

FIG. 1 shows a top view of the battery operated cautery with the safety cover in place.

FIG. 2 shows a cross-sectional side view of the battery operated cautery taken along line 2—2 of FIG. 1

FIG. 3 shows a cross-sectional end view of the battery operated cautery taken along line 3—3 of FIG. 2.

FIG. 4 shows an end view of the removable cautery safety cover.

FIG. 5 shows an end view of the battery operated cautery taken along line 5—5 of FIG. 2.

FIG. 6 shows a detailed side view of a variable temperature adjustement means.

FIG. 7 shows an end view of the variable temperature adjustment means.

Similar reference characters refer to similar parts throughout the several views of the drawings.

DETAILED DESCRIPTION OF THE PREFERRED EMBODIMENT

As shown in FIGS. 1 and 2, the present invention relates to a battery operated cautery generally indicated as 10. The battery operated cautery 10 comprises a substantially cylindrical enclosure generally indicated as 12 and a removable cautery safety cover generally indicated as 14.

The substantially cylindrical enclosure 12 is configured to retain a voltage source comprising either a single battery as shown at 16, or plurality of batteries in series. The battery 16 is biased to engage the electrode 26 of the cautery heating element 18 by a spring or other bias means engaging a retainer member 22 at the end of the enclosure 12. The cautery heating element 18 comprises a heating tip 24 extending outwardly from first and second electrodes 26 and 28, respectively, that pass through a pair of elongated apertures or channels 30 and 32, respectively, formed in a second retainer member 34. As described more fully hereinafter, the second retainer member 34 or cautery heating element retainer 34 is welded or fixedly secured to the substantially cylindrical enclosure 12.

The voltage source or batteries 16 is retained within the substantially cylindrical enclosure 12 by the first retainer element 22 engaging shoulder 36.

As best shown in FIG. 2, a conductor member generally indicated as 38 includes first and second contact elements 40 and 42, respectively, formed on opposite ends thereof and is operatively housed within the substantially cylindrical enclosure 12. The conductor member 38 is axially aligned with the longitudinal dimension of a switch actuator aperture 44 formed on the substantially cylindrical enclosure 12 and is fixed in position by fastening means 46 disposed at opposite ends thereof. A switch 48, at least partially disposed within the switch actuator aperture 44, is affixed to the forward portion of the conductor member 38 immediately adjacent the first contact element 40. The conductor member 38 is movable between a first and second position and is normally disposed in the first position with the first contact 40 out of operative engagement with the second electrode 28.

As shown if FIGS. 1 and 2, the removable safety cover 14 comprises a substantially cylindrical reduced portion 50 and an enlarged portion 52 comprising a plurality of substantially flat surfaces each indicated as 54. A groove or slot 56 including peripheral edges 58 formed on opposite sides thereof is formed on one of the substantially flat surfaces 54. The width of the groove or slot 56 is greater than the width of the base 60 of the switch actuator 48, such that when the removable safety cover 14 is operatively mounted on the substantially cylindrical enclosure 12 the peripheral edges 58 are disposed on opposite sides of the base 60 of switch actuator 48. The removable safety cover 14 further includes an insulating means comprising an insulating member 62 extending inwardly from the inner sidewall 64 thereof including an angled portion 66 and parallel portion 68. The means is configured to pass through an insulating conduit or channel 70 formed in the cautery heating element retainer 34 to normally be disposed between the first contact element 40 and the second electrode 28 when the removable safety cover 14 is operatively mounted on the substantially cylindrical enclosure 12. A switch activator housing 72 is formed on the substantially flat surface 54a. Thus the groove or slot 56, insulating member 62 and switch actuator housing 72 are aligned relative to each other.

As best shown in FIGS. 6 and 7, the instant invention may further include a variable temperature adjustment means generally indicated as 74 to permit the output temperatures of the cautery heating element 18 to be selectively varied for different medical applications. The variable temperature adjustment means 74 includes a rotatable shaft with an elongated base 76 having inner and outer reduced extensions 78 and 80 extending outwardly from opposite ends thereof. The enlarged base 76 and outer reduced extension 80 form a ledge 82 to engage the spring or bias means 20A to bias the voltage source 16 toward the second electrode 26 as best shown in FIG. 2. The inner reduced extension 78 includes a recess 84 to receive substantially cylindrical terminal means 86 which is disposed to electrically engage a terminal of the voltage source 16. The variable temperature adjustment means 74 further includes a mounting base 88 to operatively receive and support a resistance contact winding 90 electrically interconnected to the substantially cylindrical terminal contact 86 by an interconnecting conductor 92. The resistance contact winding 90 is disposed to selectively engage a reduced contact portion 94 of the conductor member 38A.

In operation, the battery operated cautery 10 is normally stored and transported with the removable safety cover 14 operatively mounted or attached to the substantially cylindrical enclosure 12 such that the peripheral sides 58 are disposed on opposite sides of the switch actuator 48. Further, the insulating means 62 prevents contact between the first contact element 40 and second electrode 28.

To use the operator initially determines the temperature or heat required for a particular application and adjusts the cautery 10 by rotating the variable temperature adjustment means 74 relative to the substantially cylindrical enclosure 12 to place a predetermined length of the resistance winding 90 in series with the heating elements. A visual indication of the output selected may be provided by an index mark formed on the outer reduced extension 80 as a pointer 96 formed on end cap member 97. with a scale printed around the exterior of the substantially cylindrical enclosure 12.

When in use, the removable safety cover 14 is removed from the substantially cylindrical enclosure 12 to permit actuation of the switch actuator 48 by depression from the first to second position such that the first contact element 40 engages the second electrode 28 completing the electrical circuit to selectively actuate the cautery heating element 18. The circuit is completed since the second contact element 42 engages the first terminal of the voltage source or battery 16 and the first electrode 26 engages the other terminal of the voltage source or battery 16.

It will thus be seen that the object set forth above and those made apparent from the preceeding description are efficiently attained and since certain changes may be made in the above construction without departing from the scope of the invention, it is intended that all the matter contained in the above description or shown in the accompanying drawings shall be interpreted as illustrative and not in a limiting sense.

It is also to be understood that the following claims are intended to cover all the generic and specific features of the invention herein described, and all statements of the scope of the invention which is a matter of language might be said to fall therebetween.

Now that the invention has been described,

What is claimed is:

1. A battery operated cautery comprising a hollow enclosure including a switch actuator aperture formed therein and configured to retain a battery voltage source including a first and second terminal, a cautery heating element mounted on one end of said hollow enclosure, a conductor member including a first contact element on one end thereof movable between a first and second position and a second contact element formed on the opposite end of said conductor member, said conductor member being operatively housed within said hollow enclosure, a switch actuator movable between a first and second position and at least partially disposed within said switch actuator aperture, affixed to said conductor member immediately adjacent said first contact element, said cautery heating element comprising a first and a second electrode at least partially disposed with said hollow enclosure and cooperatively supporting a heating tip extending outwardly from said hollow enclosure, said first contact element being normally biased in said first position in spaced relation relative to said second electrode, said first electrode being electrically connected to said first terminal of said battery voltage source, and said second contact being electrically connected to said second terminal of said battery voltage source, such that said first contact element is moved from said first and said second position by depression of said switch actuator to engage said second electrode to complete the electrical circuit thereto, and a removable safety cover to selectively cover said heating tip, said removable safety cover including an insulating member insertable between said first contact element and said second electrode of said cautery heating element when said removable safety cover is mounted on said hollow enclosure to lock said switch actuator in said first position to prevent actuation of said cautery heating element and to positively electrically insulate said first contact element from said second electrode.

2. The battery operated cautery of claim 1 further including a cautery heating element retainer fixedly secured to said hollow enclosure to secure said cautery heating element relative to said switch actuator aperture.

3. The battery operated cautery of claim 2 wherein said insulating member extends inwardly from the inner sidewall of said removable safety cover, said cautery heating element retainer further including an open-ended conduit formed therein to receive said insulating member.

4. The battery operated cautery of claim 3 wherein said insulating member comprises an angled end portion and a parallel portion extending parallel to the longitudinal axis of said hollow enclosure.

5. The battery operated cautery of claim 1 wherein said removable safety cover further includes an switch actuator housing formed on the inner portion thereof to operatively house said switch actuator when said removable safety cover is mounted on said hollow enclosure to prevent depression of said switch actuator.

6. The battery operated cautery of claim 1 further including a variable temperature adjusting resistance means electrically connected in series between said second contact element and said terminal of said battery voltage source once rotatably mountd on said hollow enclosure to vary to output temperature of said cautery heating element.

7. The battery operated cautery of claim 6 wherein said variable temperature adjustment means comprises a rotatable base having a terminal contact mounted on the inner portion thereof to electrically engage said second terminal of said battery voltage source and a resistance winding electrically interconnected to said terminal contact and disposed to selectively engage said second contact element.

8. The battery operated cautery of claim 7 wherein said second contact element has a substantially reduced cross-sectional relative to said conductor member to provide a line contact with said resistance winding.

* * * * *